(12) United States Patent
Date et al.

(10) Patent No.: US 7,060,858 B2
(45) Date of Patent: Jun. 13, 2006

(54) METHOD FOR MANUFACTURING SULFONIUM SALTS

(75) Inventors: Masashi Date, Kyoto (JP); Hideki Kimura, Kyoto (JP); Jiro Yamamoto, Kyoto (JP)

(73) Assignee: San-Apro Limited, Kyoto-Fu (JP)

( * ) Notice: Subject to any disclaimer, the term of this patent is extended or adjusted under 35 U.S.C. 154(b) by 228 days.

(21) Appl. No.: 10/450,517

(22) PCT Filed: Dec. 17, 2001

(86) PCT No.: PCT/JP01/11042

§ 371 (c)(1),
(2), (4) Date: Jun. 16, 2003

(87) PCT Pub. No.: WO02/48101

PCT Pub. Date: Jun. 20, 2002

(65) Prior Publication Data

US 2004/0030158 A1 Feb. 12, 2004

(30) Foreign Application Priority Data

Dec. 15, 2000 (JP) .............................. 2000-381963

(51) Int. Cl.
*C07C 315/00* (2006.01)
(52) U.S. Cl. .......................................... 568/18; 568/74
(58) Field of Classification Search .................. 568/18, 568/74
See application file for complete search history.

(56) References Cited

U.S. PATENT DOCUMENTS

| | | | | |
|---|---|---|---|---|
| 4,451,408 A | * | 5/1984 | Buske et al. .................. 562/73 |
| 5,021,589 A | * | 6/1991 | Wada et al. .................. 549/325 |
| 5,446,172 A | * | 8/1995 | Crivello et al. ................ 549/62 |
| 5,798,396 A | * | 8/1998 | Takahashi et al. ............. 522/15 |
| 6,111,143 A | * | 8/2000 | Park et al. ..................... 568/35 |
| 6,406,830 B1 | * | 6/2002 | Inoue et al. ............. 430/270.1 |
| 6,528,232 B1 | * | 3/2003 | Maeda et al. ............ 430/270.1 |
| 6,723,483 B1 | * | 4/2004 | Oono et al. ................. 430/170 |
| 6,818,379 B1 | * | 11/2004 | Kamabuchi et al. ...... 430/270.1 |

FOREIGN PATENT DOCUMENTS

| | | |
|---|---|---|
| EP | 455083 | 11/1991 |
| JP | 61-212554 | 9/1986 |

\* cited by examiner

*Primary Examiner*—Deborah C. Lambkin
(74) *Attorney, Agent, or Firm*—Wenderoth, Lind & Ponack, L.L.P.

(57) ABSTRACT

It is an object of the invention to provide a method which makes it possible to manufacture the desired sulfonium salts directly without using a metathesis process and without using acids in large excess amounts. An aryl compound (A) in which a hydrogen atom is bonded to at least one of the carbon atoms of the aryl group, and a sulfoxide compound (B) which can be expressed by the formula: $R^1 SO R^2$ (where $R^1$ and $R^2$ indicate hydrocarbon groups or heterocyclic groups which may be substituted, and which may be the same or different) are reacted in the presence of a strong acid (C) which can be expressed by the formula: $HMX_m Y_n$ (where M indicates an element of group IIIa or group Va of the periodic table, X indicates a halogen atom, Y indicates a hydroxyl group, m and n are integers which are such that m+n=4 and n=0 to 3 in cases where M is an element of group IIIa, and m and n are integers which are such that m+n=6 and n=0 to 2 in cases where M is an element of group Va).

8 Claims, No Drawings

METHOD FOR MANUFACTURING SULFONIUM SALTS

TECHNICAL FIELD

The present invention relates to a method for manufacturing sulfonium salts that are useful as photo-cationic polymerization initiators, photo-acid generating agents or the like, especially aryl (aromatic) group-containing sulfonium salts with polyhalo-metal, semimetal or nonmetal anions. More particularly, the present invention relates to a method for manufacturing sulfonium salts that have desired anions without using a metathesis process.

BACKGROUND ART

Conventionally, there have been various proposals regarding methods for manufacturing sulfonium salts with polyhalo-metal, semimetal or nonmetal anions. In all of these conventional manufacturing methods, a sulfoxide compound and a sulfide compound are first condensed in the presence of a strong acid such as sulfuric acid, polyphosphoric acid, methanesulfonic acid or the like so that a sulfonium salt of the strong acid used is formed; then, this reaction mixture is added to an aqueous solution of a polyhalo-metal, semimetal or nonmetal salt, i.e., $KBF_4$, $KPF_6$, $KSbF_6$, $KAsF_6$, sodium salts of the same or the like, in order for metathesis to take place, after which the desired sulfonium salt with polyhalo-metal, semimetal or nonmetal anion is recovered by filtration or the like.

Methods for forming such a sulfonium salt of a strong acid by condensing a sulfoxide compound and a sulfide compound in the presence of this strong acid include a method in which a sulfoxide compound and an aryl sulfide compound are subjected to dehydration condensation in sulfuric acid, thus forming an arylsulfonium sulfate or hydrogensulfate (see Japanese Patent Application Laid-Open No. S61-212554), a method in which a diaryl sulfide compound is partially oxidized, thus producing a mixture consisting of substantially equimolar amounts of the diaryl sulfide compound and corresponding diaryl sulfoxide, and this is then converted into a triaryl sulfonium salt using a strong acid such as sulfuric acid in the presence of a dehydrating agent such as acetic anhydride (see Japanese Patent Application Laid-Open No. S61-100557), a method in which a diaryl sulfoxide compound and a polyaryl sulfide compound are reacted in an alkylsulfonic acid (e.g., methanesulfonic acid) solution of acid anhydrides such as phosphorus penfoxide (see Japanese Patent Application Laid-Open No. H5-4996) or acetic anhydride (see Japanese Patent Application Laid-Open No. H7-82244), a method in which a diaryl sulfoxide compound and a polyaryl sulfide compound or the like are reacted in the presence of polyphosphoric acid (see Japanese Patent Application Laid-Open No. H7-82245), and the like.

However, a condensation reaction performed by the above-mentioned conventional methods, have drawbacks in yield and cost: sulfonation of aromatic rings occurs in the case of a reaction performed in sulfuric acid, so that there is a danger that the yield of the desired product will drop. Furthermore, depending on the type of aryl sulfide used, a bis-sulfonium salt may be produced even if an attempt is made to obtain a monosulfonium salt, as described in the comparative examples of the present specification: the reaction in an expensive alkylsulfonic acid such as methanesulfonic acid results in an increase in cost: side reactions occur in the case of a reaction performed in polyphosphoric acid, resulting in low yield of the desired product.

Furthermore, in all of the above-mentioned conventional methods, the reaction mixture of a sulfonium salt with the strong acid residue is added to an aqueous solution of an alkali metal polyhalo-metal, semimetal or nonmetal salt, in order for metathesis to take place. However, since polyhalo-metal, semimetal or nonmetal salts have a low solubility in water, a large amount of water must be used in order to prepare aqueous solutions of these salts. Accordingly, large quantities of waste water are generated after the desired sulfonium salt is recovered by filtration or the like. Furthermore, since this waste water contains strong acids or acetic anhydride used in excess in the reaction and is strongly acidic, it must be neutralized with caustic soda or the like before disposal, thus bringing about a problem that the amount of waste water is further increased.

The present inventors conducted diligent research in order to solve the problems encountered in conventional methods, such as a drop in yield caused by the occurrence of side reactions, the use of expensive acids, and generation of large quantities of waste water due to metathesis and neutralization. As a result, the inventors discovered a method which makes it possible to manufacture target sulfonium salts directly without using a large excess quantity of acid and without using a metathesis process. This discovery led to the present invention.

DISCLOSURE OF THE INVENTION

Specifically, the present invention is a method for manufacturing sulfonium salts with $MX_mY_n^-$ as anions, which is characterized by that an aryl compound (A) in which a hydrogen atom is bonded to at least one of the carbon atoms of the aryl group, and a sulfoxide compound (B) which can be expressed by the following formula (1)

(where $R^1$ and $R^2$ indicate hydrocarbon groups or heterocyclic groups which may be substituted, and which may be the same or different) are reacted in the presence of a strong acid (C) which can be expressed by the following formula (2)

(where M indicates an element of group IIIa or group Va of the periodic table, X indicates a halogen atom, Y indicates a hydroxyl group, m and n are integers which are such that m+n=4 and n=0 to 3 in cases where M is an element of group IIIa, and m and n are integers which are such that m+n=6 and n=0 to 2 in cases where M is an element of group Va).

In the present invention, examples of the above-mentioned aryl compound (A) in which a hydrogen atom is bonded to at least one of the carbon atoms of the aryl group include monocyclic or condensed polycyclic unsubstituted aryl compounds, e.g., benzene, naphthalene, anthracene, phenanthrene, naphthacene and pyrene; aryl compounds that are substituted by alkyl groups, e.g., toluene, cumene, tert-butylbenzene, xylene, ethylbenzene, dodecylbenzene, 1-methylnaphthalene and 1H-indene; aryl compounds that are substituted by aryl groups, e.g., biphenyl, biphenylene, 1,2'-binaphthyl and 2-phenylnaphthalene; aryl compounds that are substituted by nitro groups, nitrile groups, hydroxyl groups, halogen atoms, or the like, e.g., nitrobenzene, benzonitrile, phenol, chlorobenzene and fluorobenzene; aryl compounds substituted by alkoxy groups which may in turn be substituted, e.g., anisole, ethoxybenzene, 1-methoxynaphthalene, benzylphenyl ether and benzofuran; aryl compounds substituted by aryloxy groups which may in turn be substituted, e.g., diphenyl ether, 2-ethoxynaphthalene, 4-phenoxyphenol and xanthene; aryl compound substituted by alkylsulfonyl groups, e.g., methylphenylsulfone; aryl compounds substituted by arylsulfonyl groups, e.g., diphenylsulfone; aryl compounds substituted by acyl groups which may in turn be substituted, e.g., acetophenone, acetylacetophenone and 2-phenylacetophenone; aryl compounds substituted by aroyl groups which may in turn be substituted, e.g., benzophenone, 4-methylbenzophenone and xanthone; aryl compounds substituted by alkylthio groups which may in turn be substituted, e.g., thioanisole, ethylthiobenzene, benzothiophene, benzylphenyl sulfide and phenacylphenyl sulfide; and aryl compounds substituted by arylthio groups which may in turn be substituted, e.g., diphenyl sulfide, dibenzothiophene, (2-methylphenyl)phenyl sulfide, (4-methylphenyl)phenyl sulfide, 2,2'-ditolyl sulfide, 2,3'-ditolyl sulfide, 2-phenylthionaphthalene, 9-phenylthioanthracene, (3-chlorophenyl)phenyl sulfide, (4-chlorophenyl)phenyl sulfide, 3,3'-dichlorodiphenyl sulfide, (3-bromophenyl)phenyl sulfide, 2,2'-dibromodiphenyl sulfide, 3,3'-dibromodiphenyl sulfide, (2-methoxyphenyl)phenyl sulfide, phenoxathiin, thioxanthone, 2-isopropylthioxanthone, 2-methoxythioxanthone, 4,4'-diphenylthiobenzophenone, 4,4'-diphenylthiodiphenyl ether, 4,4'-diphenylthiobiphenyl, (4-phenylthiophenyl)phenyl sulfide, (4-phenylthiophenyl)diphenylsulfonium salts (hexafluorophosphate, hydrogensulfate, sulfate, methanesulfonate and the like), (4-benzoylphenyl)phenyl sulfide, (2-chloro-4-benzoylphenyl) phenyl sulfide, (2-methylthiobenzoylphenyl)phenyl sulfide and the like.

Desirable compounds among these aryl compounds (A) include monocyclic or condensed polycyclic unsubstituted aryl compounds, aryl compounds substituted by hydroxyl groups or halogen atoms, and aryl compounds substituted by alkyl groups, aryl groups, alkyloxy groups, aryloxy groups, acyl groups, aroyl groups, alkylthio groups or arylthio groups (all of which may in turn be substituted), and even more desirable are unsubstituted aryl compounds, aryl compounds substituted by hydroxyl groups or halogen atoms, and aryl compounds substituted by alkyl groups, alkyloxy groups, aroyl groups or arylthio groups, which may in turn be substituted.

In particular, benzene, phenol, chlorobenzene, fluorobenzene, toluene, tert-butylbenzene, anisole, benzophenone, 4-methylbenzophenone, diphenyl sulfide, (4-chlorophenyl) phenyl sulfide, 2-phenylthionaphthalene, 9-phenylthioanthracene, (4-phenylthiophenyl)phenyl sulfide, 4,4'-diphenylthiobiphenyl, (4-benzoylphenyl)phenyl sulfide, (2-chloro-4-benzoylphenyl) phenyl sulfide, 4,4'-diphenylthiobenzophenone, thioxanthone and 2-isopropylthioxanthone are especially desirable. These compounds may be used singly, or may be used in combinations consisting of two or more compounds.

In sulfoxide compounds (B) expressed by the formula

(1)

$R^1$ and $R^2$ in the formula indicate hydrocarbon groups or heterocyclic groups that may be substituted; these groups may be the same or different. Examples of $R^1$ and $R^2$ include alkyl groups such as methyl groups, ethyl groups, butyl groups, octyl groups and the like; cycloalkyl groups such as cyclopentyl groups, cyclohexyl groups and the like; aryl groups such as phenyl groups, naphthyl groups, anthryl groups and the like; and aromatic heterocyclic groups such as pyridyl groups, furfuryl groups and the like. Furthermore, $R^1$ and $R^2$ may be bonded to each other to form a ring such as a tetramethylene group.

$R^1$ and $R^2$ may be substituted; examples of substituent groups that can be used include alkyl groups such as methyl groups, ethyl groups and the like; aryl groups such as phenyl groups, naphthyl groups, anthryl groups and the like; alkyloxy groups such as methoxy groups and the like; aryloxy groups such as phenoxy groups and the like; alkylthio groups such as methylthio groups and the like; arylthio groups such as phenylthio groups and the like; acyl groups such as acetyl groups and the like; aroyl groups such as benzoyl groups and the like; acyloxy groups such as acetoxy groups and the like; and aroyloxy groups such as benzoyloxy groups and the like; as well as nitrile groups, nitro groups, hydroxyl groups, halogen atoms and the like.

Examples of such sulfoxide compounds (B) include dimethyl sulfoxide, methylethyl sulfoxide, tetramethylene sulfoxide, diphenyl sulfoxide, dibenzothiophene-S-oxide, (4-methylphenyl)phenyl sulfoxide, 4,4'-dimethyldiphenyl sulfoxide, 4,4'-dimethoxydiphenyl sulfoxide, 4-methylthiodiphenyl sulfoxide, (4-phenylthiophenyl)phenyl sulfoxide, 4,4'-dihydroxydiphenyl sulfoxide, 4,4'-difluorordiphenyl sulfoxide, 4,4'-dichlorodiphenyl sulfoxide and the like. These compounds may be used singly, or may be used in combinations consisting of two or more compounds.

Desirable compounds among these sulfoxide compounds (B) are those in which $R^1$ and $R^2$ are aryl groups which may be substituted. Especially desirable are diphenyl sulfoxide, 4,4'-dimethyldiphenyl sulfoxide, 4,4'-dimethoxydiphenyl sulfoxide, 4,4'-dihydroxydiphenyl sulfoxide, 4,4'-difluorodiphenyl sulfoxide and 4,4'-dichlorodiphenyl sulfoxide.

The sulfoxide compound (B) that is used may be a commercial product or a separately synthesized compound; if necessary, furthermore, this compound may be produced in situ by a reaction of the corresponding sulfide compound with a peroxide such as hydrogen peroxide or the like.

In the formula $HMX_mY_n$ (2) which expresses the strong acid (C) of the present invention, M indicates an element selected from group IIIa (boron, aluminum or the like) or group Va (phosphorus, arsenic, antimony, bismuth or the like) of the periodic table, X indicates a halogen selected from fluorine, chlorine, bromine and the like, and Y indicates a hydroxyl group: m and n are integers which are such that m+n=4 and n=0 to 3 in cases where M is an element of group IIIa, and which are such that m+n=6 and n=0 to 2 in cases where M is an element of group Va.

Examples of such strong acids (C) include compounds expressed by the formulae $HBF_4$, $HBF_3(OH)$, $HBF_2(OH)_2$, $BF(OH)_3$, $HAlCl_4$, $HPF_6$, $HPF_5(OH)$, $HPF_4(OH)_2$, $HPCl_6$, $HPBr_6$, $HAsF_6$, $HSbCl_6$, $HSbF_6$, $HSbF_5(OH)$, $HSbF_4(OH)_2$, $HBiF_6$ and the like. These compounds may be used singly or in combinations consisting of two or more compounds.

Desirable compounds among these strong acids (C) are $HBF_4$, $HPF_6$, $HAsF_6$ and $HSbF_6$, and especially desirable are $HBF_4$, $HPF_6$ and $HSbF_6$.

The strong acids (C) may be used "as is", or may be used in the form of a complex such as a hydrate or diethyl ether complex or the like, or in the form of an aqueous solution or a solution in an organic acid such as acetic acid or the like or in an organic solvent such as diethyl ether or the like.

The strong acid (C) used may be a commercial product; alternatively, it may be generated in situ either prior to or during the reaction of the aryl compound (A) and sulfoxide compound (B), or may be prepared outside the reaction system.

Methods which can be used to generate such strong acids (C) include one in which fluorides such as $BF_3$, $PF_5$, $AsF_5$, $SbF_5$ or the like are reacted with hydrogen fluoride, one in which alkali metal or alkaline earth metal salts of $HMX_mY_n$, such as $LiBF_4$, $NaBF_4$, $KBF_4$, $Ba(BF_4)_2$, $LiPF_6$, $NaPF_6$, $KPF_6$, $LiSbF_6$, $NaSbF_6$, $KSbF_6$ or the like are reacted with inorganic acids such as sulfuric acid, phosphoric acid, hydrochloric acid or the like, and one in which oxides such as $B_2O_3$, $P_2O_5$, $Sb_2O_5$ or the like are reacted with hydrogen fluoride (for example, such methods are described in "Supplement to MELLOR'S COMPREHENSIVE TREATISE ON INORGANIC AND THEORETICAL CHEMISTRY", Vol. VIII, Supplement III, Phosphorus, Section XXXI (LONGMAN, 1971)" and the like).

Among the above-mentioned methods, the one in which fluorides such as $BF_3$, $PF_5$, $SbF_5$ or the like are reacted with hydrogen fluoride, and the one in which alkali metal or alkaline earth metal salts of $HMX_mY_n$ are reacted with inorganic acids such as sulfuric acid, phosphoric acid, hydrochloric acid or the like, especially the method in which $NaBF_4$, $NaPF_6$, $NaSbF_6$ or K salts of the same are reacted with sulfuric acid, are convenient and desirable.

For example, as methods in which fluorides such as $BF_3$, $PF_5$, $SbF_5$ or the like are reacted with hydrogen fluoride, after a gas of $BF_3$ or $PF_5$ is blown into, ordinarily under cooling at a temperature of 0 to 30° C., or a liquid such as $SbF_5$ is added dropwise to a non-reactive solvent such as diethyl ether, so that a fluoride solution is formed, ordinarily an equimolar amount of hydrogen fluoride is, at a temperature of 0 to 30° C. under cooling, either blown in in the form of a gas by heating with a water bath, or added dropwise in liquid form by cooling at about 0 to 10° C.

In the above-mentioned reaction, the molar ratio of the fluoride such as $BF_3$, $PF_5$, $SbF_5$ or the like to diethyl ether is ordinarily 1:1 or greater, preferably 1:2 or greater. If the molar ratio of diethyl ether to the fluoride is smaller than 1, there is a danger that the excess amount of fluoride will diffuse out of the system as a gas. There is no particular upper limit to the amount of diethyl ether; ordinarily, however, the amount used is 10 moles or less, preferably 6 moles or less, per mole of fluoride.

The reaction molar ratio of the fluoride such as $BF_3$, $PF_5$, $SbF_5$ or the like to the above-mentioned hydrogen fluoride is ordinarily 1:0.8 to 1:1.2, and is preferably 1:1.

For example, methods for reacting the alkali metal or alkaline earth metal salt of $HMX_mY_n$ with an inorganic acid such as sulfuric acid, phosphoric acid, hydrochloric acid or the like include one in which such salts are first dissolved or dispersed in water, an organic acid such as acetic acid or the like, an organic acid anhydride such as acetic anhydride or the like, or a polar organic solvent such as acetonitrile or the like, and then the inorganic acid is added dropwise and reacted.

The above-mentioned alkali metal or alkaline earth metal salt of $HMX_mY_n$ and sulfuric acid are used ordinarily in theoretical amounts; however, good results can be obtained even if the amount of acid is varied within the range of 0.5 to 4 times the theory. For example, the theoretical amount of sulfuric acid in the case of a reaction of $NaPF_6$ and sulfuric acid is 1 mole of sulfuric acid per mole of $NaPF_6$; however, the amount of sulfuric acid may be varied in the range of 0.5 to 4.0 moles. In cases where the amount of sulfuric acid is less than 0.5 moles relative to 1 mole of $NaPF_6$, there may be instances where the required amount of $HPF_6$ is not generated. On the other hand, in cases where the amount of sulfuric acid exceeds 4.0 moles, sulfonation of the aryl compound (A) or sulfoxide compound (B) occurs, and the amount of waste acid is increased; accordingly, such a large amount is undesirable. The concentration of the sulfuric acid is 20% or greater, preferably 50% or greater, and even more preferably 70% or greater.

The reaction temperature during this reaction is ordinarily 0 to 80° C., and is preferably 20 to 60° C.

In the reaction of the present invention, the molar ratio of the aryl compound (A) and sulfoxide compound (B) is ordinarily 1:(0.9 to 3.0), and is preferably 1:(1.0 to 2.1). If the amount of the sulfoxide compound (B) is less than 0.9 moles per mole of the aryl compound (A), the yield of the desired sulfonium salt decreases. On the other hand, if this amount exceeds 3.0 moles, an unnecessarily large amount of the sulfoxide compound (B) is being used, resulting in higher cost.

The molar ratio of the sulfoxide compound (B) and strong acid (C) is ordinarily 1:(0.9 to 3.0), and is preferably 1:(1.0 to 1.5). If the amount of strong acid (C) is less than 0.9 moles per mole of the sulfoxide compound (B), the yield of the desired sulfonium salt decreases. On the other hand, if this amount exceeds 3.0 moles, the amount of waste acid is increased, resulting in higher cost.

The reaction of the present invention is a dehydration condensation between the above-mentioned aryl compound (A) and sulfoxide compound (B). Thus, if an excess amount of water is present in the reaction mixture, the reaction is slowed down and the yield is decreased. If necessary, therefore, the reaction of the present invention may be performed in the presence of a dehydrating agent (D). Examples of dehydrating agents (D) that can be used include inorganic oxides such as phosphorus pentoxide, phosphorus oxychloride and the like, inorganic acids such as polyphosphoric acid and the like, and organic acid anhydrides such as acetic anhydride, propionic anhydride, phthalic anhydride and the like. These dehydrating agents (D) may be used singly, or may be used in combinations consisting of two or more agents. Desirable agents among these dehydrating agents (D) are organic acid anhydrides such as acetic anhydride and the like, and acetic anhydride is especially desirable.

The dehydrating agent (D) is used in such an amount that the water content of the reaction mixture of the aryl compound (A) and sulfoxide compound (B) is 7% or less, preferably 5% or less, and even more preferably 3% or less. The "water content of the reaction mixture" refers to the sum of the water present in cases where an aqueous solution or hydrate is used as the strong acid (C), the water in the sulfuric acid that is used to produce the strong acid (C), the water in the solvent, the water that is produced by the reaction of the aryl compound (A) and sulfoxide compound (B), and the like.

The reaction of the present invention may also be performed in the presence of a solvent. Examples of solvents that can be used include ethers such as diethyl ether and the like, chlorinated organic solvents such as dichloromethane and the like, alcohols such as methanol, ethanol and the like, ketones such as acetone and the like, organic acids such as acetic acid and the like, organic acid anhydrides such as acetic anhydride, propionic anhydride and the like, and polar organic solvents such as acetonitrile and the like. These solvents may be used singly, or may be used in combinations consisting of two or more solvents. Desirable among these solvents are ethers such as diethyl ether and the like, chlorinated organic solvents such as dichloromethane and the like, organic acids such as acetic acid and the like, organic acid anhydrides such as acetic anhydride, propionic anhydride and the like, and polar solvents such as acetonitrile and the like; furthermore, diethyl ether, dichloromethane, acetic acid, acetic anhydride and acetonitrile are especially desirable.

The amount of solvent used is ordinarily 0 to 80 wt %, based on the total weight of the aryl compound (A), sulfoxide compound (B), strong acid (C), dehydrating agent (D), and solvent.

In the present invention, there are no particular restrictions on the order of additions of the respective raw materials to the reaction vessel. Ordinarily, however, the dehydrating agent (D) and/or solvent are added first; then, the sulfoxide compound (B) is added, mixed and dissolved, after which the strong acid (C) is gradually added, followed by the aryl compound (A).

In cases where the strong acid (C) is produced in situ, for example, a solvent such as water, acetic acid, acetic anhydride, acetonitrile or the like is added to the vessel first. Then, a reaction that produces the strong acid (C) is performed, after which the sulfoxide compound (B) is added to this solution, mixed and dissolved, followed by addition of the aryl compound (A), solvent and, if necessary, dehydrating agent (D). Alternatively, the raw materials used to produce the strong acid (C) may be added after the aryl compound (A), sulfoxide compound (B), solvent and, if necessary, dehydrating agent (D) have been added.

The reaction temperature in the present invention is ordinarily −30° C. to 120° C., preferably 0° C. to 100° C., and even more preferably 10 to 80° C.

The reaction time depends on the reaction temperature, reaction concentration and degree of agitation; ordinarily, however, the reaction time is 0.5 to 24 hours, and is preferably 1 to 10 hours.

In the present invention, the dehydrating agent and the solvent used, such as an organic acid anhydride, acetic acid, diethyl ether or the like, can easily be recovered by distillation at ordinary pressure or under reduced pressure after the reaction.

The temperature of recovery of these materials is ordinarily 40 to 120° C., and is preferably 50 to 80° C. If the temperature exceeds 120° C., there is a danger that the desired sulfonium salt decomposes. The recovered dehydrating agent and solvents can be reused.

The method used to recover the desired sulfonium salt from the reaction mixture in the present invention varies according to the properties of the sulfonium salt obtained. For example, first, water is added to the reaction mixture, or the reaction mixture is added to water in order to deposit the target material: and if this deposited substance is a solid, a method may be used, in which the product is collected by filtration, washed with water and then dried. When the deposited substance is a liquid, a method may be employed where the target substance is extracted with an organic solvent such as dichloromethane, ethyl acetate or the like, and the separated organic layer is washed with water, concentrated and dried. If necessary, the purity of the sulfonium salt that is obtained can be improved by washing with an alcohol such as methanol, ethanol or the like, a ketone such as acetone or the like, or a chlorinated organic solvent such as dichloromethane or the like, or by recrystallization from these solvents.

Sulfonium salts obtained by the manufacturing method of the present invention can be used as photo-cationic polymerization initiators, photo-acid generating agents for resists, thermally latent curing accelerators for epoxy resins, etc.

The present invention will be further described below in terms of examples; however, the present invention is not limited to these examples.

EXAMPLE 1

In a 100-ml reaction vessel were placed 4.05 g (20.0 mmol) of diphenyl sulfoxide, 4.05 g of acetic acid and 5.67 g (29.1 mmol) of a 75% aqueous solution of hexafluorophosphoric acid and, under cooling, 13.99 g (137 mmol) of acetic anhydride was gradually added dropwise, and the mixture was stirred for 30 minutes. Then, after adjusting the temperature of this solution to room temperature, 3.61 g (19.4 mmol) of diphenyl sulfide was added dropwise, and the reaction mixture was stirred for 1 hour at room temperature (reaction concentration: 24%).

The temperature of this reaction mixture was elevated to 70° C., and 4.5 g of solvent consisting mainly of acetic acid was recovered under reduced pressure.

After cooling to room temperature, the contents were dissolved in 20 ml of dichloromethane, and the solution was washed once with 20 ml of water, and additionally three times with 10 ml each of water. The dichloromethane was distilled off from the organic layer, thus producing 9.73 g (yield: 97%) of a somewhat yellowish tarry substance. When the waste water from washing was neutralized, 23 g of a 40% aqueous sodium hydroxide was required.

It was confirmed by $^{13}$C-NMR and IR analysis that this tarry material consisted of (4-phenylthiophenyl)diphenylsulfonium hexafluorophosphate, and contained raw-materials, i.e., diphenyl sulfide and diphenyl sulfoxide, as impurities. Analysis by HPLC showed that the purity was 94%.

When 10 ml of ethanol was added to this tarry material and the resulting mixture was agitated, crystals precipitated. These crystals were collected by filtration and dried, to give 8.96 g of white powder (purified product). The purity was more than 99%.

EXAMPLE 2

In a 100-ml reaction vessel were placed 5.36 g (29.1 mmol) of potassium hexafluorophosphate and 5.36 g of acetic acid and were mixed by stirring. Then, 2.91 g (29.1 mmol) of concentrated sulfuric acid was added, and the reaction mixture was stirred for 30 minutes.

To this solution was added, at room temperature, a uniform solution of 4.05 g (20.0 mmol) of diphenyl sulfoxide and 5.94 g (58.2 mmol) of acetic anhydride prepared beforehand, followed by dropwise addition of 3.61 g (19.4 mmol) of diphenyl sulfide (reaction concentration: 28%). After this mixture was aged for 1 hour at 45° C., 5.1 g of solvent consisting mainly of acetic acid was recovered at 65° C. under reduced pressure.

After cooling to room temperature, 20 ml of dichloromethane and 20 ml of water were added to get the reaction mixture dissolved, and washed. The layers were separated and the organic layer was additionally washed three times with 10 ml each of water, and dichloromethane was then distilled off, producing 9.83 g (yield: 98%) of a slightly yellowish solid material. The wash water was neutralized with 11 g of a 40% aqueous caustic soda.

$^{13}$C-NMR analysis and IR analysis showed that the solid material thus obtained contained the desired (4-phenylthiophenyl)diphenylsulfonium hexafluorophosphate and small amounts of raw materials. Results of HPLC analysis indicated that the purity was 96%.

This solid substance was treated with 10 ml of ethanol and dried, thus producing 9.15 g of a white powder. The purity was better than 99%.

EXAMPLE 3

The same procedure as in Example 2, except that 4.24 g (25.2 mmol) of sodium hexafluorophosphate was used instead of potassium hexafluorophosphate, and 4.24 g of acetonitrile was used instead of acetic acid, afforded 9.80 g (yield: 98%) of a somewhat yellowish solid material. Solvent (4.1 g) consisting mainly of acetonitrile was recovered, and the wash water was neutralized with 10 g of 40% aqueous caustic soda.

$^{13}$C-NMR analysis and IR analysis indicated that the solid substance thus obtained contained the desired (4-phenylthiophenyl)-diphenylsulfonium hexafluorophosphate and small amounts of raw materials. Results of HPLC analysis showed that the purity was 95%.

This solid substance was treated with 10 ml of ethanol and dried, to give 9.05 g of a white powder. The purity was more than 99%.

EXAMPLE 4

In a 100-ml reaction vessel were placed 10 ml of diethyl ether and 4.33 g (20.0 mmol) of antimony pentafluoride and these were uniformly mixed. Then, 0.40 g (20.0 mmol) of hydrogen fluoride was added dropwise at 5° C. To this solution was dropwise added at 10° C., a solution of 4.07 g (20.0 mmol) of diphenyl sulfoxide, 3.73 g (20.0 mmol) of diphenyl sulfide and 2.04 g (20.0 mmol) of acetic anhydride dissolved beforehand in 10 ml of diethyl ether (reaction concentration: 27%). After stirring for 30 minutes, the reaction was carried out for 1 hour at 35° C.

To the reaction mixture was added 20 ml of water, and diethyl ether was distilled off at ordinary pressure. Then the reaction solution was neutralized by gradually adding 2 g of 40% aqueous caustic soda and the solid substance which precipitated was collected by filtration. This substance was washed twice with 10 ml of water and dried to give 11.5 g (yield: 95%, purity: 96%) of white solid material.

It was confirmed by $^{13}$C-NMR and IR analysis that the solid thus obtained was the desired (4-phenylthiophenyl)diphenylsulfonium hexafluoroantimonate.

EXAMPLE 5

The same procedure as in Example 2, except that 5.86 g (21.3 mmol) of potassium hexafluoroantimonate was used instead of potassium hexafluorophosphate, and 5.86 g of acetonitrile was used instead of acetic acid, afforded 11.56 g (yield: 98%, purity: 94%) of slightly yellow solid substance. In this case, 5.7 g of solvent consisting mainly of acetonitrile was recovered, and the wash water was neutralized with 10 g of 40% aqueous caustic soda.

$^{13}$C-NMR analysis and IR analysis indicated that the solid substance obtained contained small amounts of raw materials.

This tar-form substance was treated with 10 ml of ethanol and dried, thus producing 10.4 g of a white powder. The purity was more than 99%.

EXAMPLE 6

The same procedure as in Example 3, except that 5.63 g (19.4 mmol) of (4-benzoyl)diphenyl sulfide was used instead of diphenyl sulfide, and 4.77 g (20.0 mmol) of 4,4'-difluorodiphenyl sulfoxide was used instead of diphenyl sulfoxide, afforded 11.71 g of product. The yield was 92%, and the purity was 95%.

EXAMPLE 7

In a 100-ml reaction vessel were placed 5.86 g (21.3 mmol) of potassium hexafluoroantimonate, 9.90 g (97.0 mmol) of acetic anhydride and 6.40 g (64.0 mmol) of concentrated sulfuric acid and were mixed by stirring. Then, 4.61 g (20.0 mmol) of 4,4'-dimethyldiphenyl sulfoxide was added, and the resulting mixture was stirred for 30 minutes.

To this solution was added a solution prepared beforehand by dissolving 4.92 g (19.4 mmol) of 2-isopropylthioxanthone in 4.92 g of acetic acid with heating. After this mixture was allowed to react for 2 hours at 45° C., 4.9 g of solvent consisting mainly of acetic acid was recovered under reduced pressure at 65° C.

This reaction mixture was cooled to room temperature, and 20 ml of dichloromethane and 30 ml of water were added. The solution was neutralized with 19 g of 40% aqueous sodium hydroxide under cooling, and waste water was removed. The organic layer was washed three more times with 10 ml each of water, and dichloromethane was distilled off to give 9.83 g (yield: 94%, purity: 95%) of yellow solid.

The solid material obtained was the desired 4,4'-dimethyldiphenylsulfonium hexafluoroantimonate of 2-isopropylthioxanthone.

EXAMPLE 8

The same procedure as in Example 5, except that 2.10 g (19.4 mmol) of anisole was used instead of diphenyl sulfide, and 5.52 g (21.3 mmol) of sodium hexafluoroantimonate was used instead of potassium hexafluoroantimonate, afforded 9.45 g (yield: 92%, purity: 95%) of slightly brown solid. The solid material obtained was (4-methoxyphenyl)diphenylsulfonium hexafluoroantimonate.

EXAMPLE 9

The same procedure as in Example 2, except that 3.20 g (29.1 mmol) of sodium tetrafluoroborate was used instead of potassium hexafluorophosphate, afforded 8.28 g (yield: 93%, purity: 94%) of desired (4-phenylthiophenyl) diphenylsulfonium tetrafluoroborate as solid.

COMPARATIVE EXAMPLE 1

In a 100-ml reaction vessel were placed 20 ml (36.8 g, 368 mmol) of concentrated sulfuric acid and 2.05 g (10.1 mmol) of diphenyl sulfoxide and dissolved. To this solution was added dropwise 1.80 g (9.7 mmol) of diphenyl sulfide over a period of 2 minutes at room temperature, and stirring was continued for 1 hour (reaction concentration: 9.5%).

Separately, 60 g of ice was added to a solution prepared beforehand by dissolving 1.87 g (10.2 mmol) of potassium hexafluorophosphate in 60 ml of water, and to this was gradually added the above-mentioned reaction mixture under ice water cooling, whereupon white solid deposited.

The white solid was separated by filtration, washed four times with 10 ml each of water and dried under reduced pressure, to afford 3.3 g of white powder. When the waste water from filtration and wash water was neutralized, 71 g of 40% aqueous sodium hydroxide was required.

$^{13}$C-NMR and IR analysis of the white power obtained showed that it contained (4-phenylthiophenyl)bisdiphenylsulfonium bishexafluorophosphate with two sulfonio groups, and impurities of unknown structure, instead of the expected (4-phenylthiophenyl)diphenylsulfonium hexafluorophosphate with one sulfonio group. The yield of the disulfonium salt obtained was 80%, and the purity was 90%. Furthermore, when the filtrate from the above-mentioned filtration was analyzed, it was confirmed that this filtrate contained sulfonated diphenyl sulfide.

COMPARATIVE EXAMPLE 2

In a 100-ml reaction vessel were placed 7.9 g (77 mmol) of acetic anhydride, 43.0 g (447 mmol) of methanesulfonic acid, 12.12 g (60 mmol) of diphenyl sulfoxide and 9.3 g (50 mmol) of diphenyl sulfide, uniformly dissolved (reaction concentration: 30%), and then, reacted at 80° C. for 6 hours. After being cooled to room temperature, the reaction mixture was added dropwise to 300 ml of water under ice water cooling; then, 9.5 g (52 mmol) of potassium hexafluorophosphate was added, and the mixture was stirred for 1 hour.

Brown crystals which deposited were collected by filtration, washed three times with 50 ml each of water, dried under reduced pressure to give 25.3 g (yield: 98%, purity: 63%) of brown solid. When the waste water from filtration and wash water were neutralized, 52 g of 40% aqueous sodium hydroxide was required.

$^{13}$C-NMR and IR analysis of the brown solid obtained showed that the main component was (4-phenylthiophenyl)diphenylsulfonium hexafluorophosphate, and that the impurities included (4-phenylthiophenyl) bisdiphenylsulfonium bishexafluorophosphate, small amounts of the raw materials, and compounds of unknown structure.

COMPARATIVE EXAMPLE 3

To a solution of 19.5 g (191 mmol) of acetic anhydride and 106.2 g (965 mmol) of ethanesulfonic acid, 29.0 g (100 mmol) of (4-benzoyl)diphenyl sulfide and 23.9 g (100 mmol) of 4,4'-difluorodiphenyl sulfide were added, and reacted for 7 hours with the temperature being elevated to 80° C. Next, the reaction mixture was poured into 300 ml of water; then, 16.8 g (100 mmol) of sodium hexafluorophosphate was added, and the mixture was stirred for 1 hour.

The solid which deposited was collected by filtration, washed five times with 50 ml each of water, and then dried under reduced pressure to give brown solid (amount; 55.8 g, yield: 85%, purity: 80%). When the waste water from filtration and wash water were neutralized, 119 g of 40% aqueous sodium hydroxide was required.

$^{13}$C-NMR and IR analysis of the brown solid obtained showed that the main component was (4-benzoylphenyl)thiophenyl-4,4'-difluorodiphenylsulfonium hexafluorophosphate, and that this contained 4,4'-difluorodiphenyl sulfoxide, (4-benzoyl)diphenyl sulfide and impurities of unknown structure as impurities.

COMPARATIVE EXAMPLE 4

To a solution of 750 g (7.35 mmol) of acetic anhydride and 250 g (2.50 mmol) of sulfuric acid, 127 g (0.50 mmol) of 2-isopropylthioxanthone was added. Then, 115 g (0.50 mmol) of 4,4'-dimethyldiphenyl sulfoxide was added in portions over a period of about 2.5 hours with the solution temperature adjusted to 40° C. Next, after a reaction for 2.5 hours at 40° C., a further reaction was carried out for 2.5 hours at 45° C. Then, the reaction mixture was poured into 2 liters of water, and was neutralized with 1700 g of 40% aqueous sodium hydroxide and allowed to stand.

After the aqueous layer was discarded, 2.5 liters of water was added, followed by addition of 25 g of activated carbon. After the mixture was stirred for 1 hour at 50° C., the mixture was filtered, and 1200 g of toluene was added to the filtrate. Then, 124 g (0.45 mol) of potassium hexafluoroantimonate was added in small portions, and the mixture was stirred for 20 minutes and then allowed to stand. The aqueous layer was then discarded. To the toluene layer was added 1000 g of 15% aqueous sodium chloride and this layer was washed. After aqueous layer was removed, toluene was distilled off at about 60° C. under reduced pressure to give 275 g of yellow solid (yield: 78%, purity: 88%).

$^{13}$C-NMR and IR analysis of the yellow solid obtained showed that the main component was 4,4'-dimethyldiphenylsulfonium hexafluoroantimonate of 2-isopropylthioxanthone; peaks arising from 4,4'-difluorodiphenyl sulfoxide and 2-isopropylthioxanthone were also detected as impurities.

The results obtained in Examples 1 through 9 and Comparative Examples 1 through 4 are shown in Table 1. It is seen from this table that the manufacturing method of the present invention affords the desired sulfonium salts of better purity in higher yields, and generates less amount of waste water than the conventional methods.

TABLE 1

| | | Reaction product*[1] | | Amount of waste water per kg of target substance in the reaction product*[1] | | | |
|---|---|---|---|---|---|---|---|
| | | Yield (%) | Purity (%) | Amount of water used in metathesis (kg) | Amount of wash water (kg) | Amount of aqueous NaOH solution required to neutralize waste water (kg) | Total (kg) |
| Example | 1 | 97 | 94 | 0 | 5.5 | 2.5 | 8.0 |
| | 2 | 98 | 96 | 0 | 5.3 | 1.2 | 6.5 |
| | 3 | 98 | 95 | 0 | 5.4 | 1.1 | 6.5 |
| | 4 | 95 | 96 | 0 | 3.5 | 0.2 | 3.7 |
| | 5 | 98 | 94 | 0 | 4.6 | 0.9 | 5.5 |
| | 6 | 92 | 95 | 0 | 4.5 | 0.9 | 5.4 |
| | 7 | 94 | 95 | 0 | 4.9 | 2.2 | 7.1 |
| | 8 | 92 | 95 | 0 | 5.6 | 1.1 | 6.7 |
| | 9 | 93 | 94 | 0 | 6.4 | 1.4 | 7.8 |

TABLE 1-continued

| | | Reaction product[1] | | Amount of waste water per kg of target substance in the reaction product[1] | | Amount of aqueous NaOH solution | |
|---|---|---|---|---|---|---|---|
| | | Yield (%) | Purity (%) | Amount of water used in metathesis (kg) | Amount of wash water (kg) | required to neutralize waste water (kg) | Total (kg) |
| Comparative | 1[2] | 80 | 90 | 40.4 | 13.5 | 23.9 | 77.8 |
| Example | 2 | 98 | 63 | 18.9 | 9.4 | 3.3 | 31.6 |
| | 3 | 85 | 80 | 6.7 | 5.6 | 2.7 | 15.0 |
| | 4 | 78 | 88 | 10.3 | 12.4 | 7.0 | 29.7 |

[1] Not purified
[2] Values for disulfonium salt obtained (desired mono-sulfonium salt was not obtained)

INDUSTRIAL APPLICABILITY

The method of the present invention for manufacturing sulfonium salt possesses the following advantages:
1. Desired sulfonium salts can be manufactured in high purity and high yields.
2. Because strong acids are not used in large amounts and dehydrating agents and solvents, such as acetic anhydride and acetic acid that are used, can be recovered, the amount of alkali required for neutralization of the waste water can be reduced.
3. Because there is no metathesis process, the amount of waste water generated can be greatly reduced.

What is claimed is:

1. A method for manufacturing sulfonium salts with $MX_mY_n^-$ as anions which is characterized by that an aryl compound (A) in which a hydrogen atom is bonded to at least one of the carbon atoms of the aryl group, and a sulfoxide compound (B) which can be expressed by the following formula (1):

(1)

(where $R^1$ and $R^2$ indicate hydrocarbon groups or heterocyclic groups which may be substituted, and which may be the same or different) are reacted in the presence of a strong acid (C) which can be expressed by the following formula (2)

$$HMX_mY_n \quad (2)$$

(where M indicates an element of group IIIa or group Va of the periodic table, X indicates a halogen atom, Y indicates a hydroxyl group, m and n are integers which are such that m+n=4 and n=0 to 3 in cases where M is an element of group IIIa, and m and n are integers which are such that m+n=6 and n=0 to 2 in cases where M is an element of group Va),
wherein the reaction is performed in the presence of a dehydrating agent (D).

2. The manufacturing method according to claim 1, wherein the aryl compound (A) has an arylthio group and/or an aroyl group which may be substituted.

3. The manufacturing method according to claim 1, wherein $R^1$ and $R^2$ of the sulfoxide compound (B) are aryl groups which may be substituted.

4. The manufacturing method according to claim 1, wherein the strong acid (C) is at least one acid selected from $HBF_4$, $HPF_6$ and $HSbF_6$.

5. The manufacturing method according to claim 4, wherein the strong acid (C) is generated by a reaction of a $BF_4$, $PF_6$ or $SbF_6$ salt of an alkali or alkaline earth metal with sulfuric acid.

6. The manufacturing method according to claim 2, wherein $R^1$ and $R^2$ of the sulfoxide compound (B) are aryl groups which may be substituted.

7. The manufacturing method according to claim 2, wherein the strong acid (C) is at least one acid selected from $HBF_4$, $HPF_6$ and $HSbF_6$.

8. The manufacturing method according to claim 3, wherein the strong acid (C) is at least one acid selected from $HBF_4$, $HPF_6$ and $HSbF_6$.

* * * * *